US010834896B2

(12) United States Patent
Lin et al.

(10) Patent No.: US 10,834,896 B2
(45) Date of Patent: Nov. 17, 2020

(54) METHOD FOR TAGGING INSECTS AND ARTHROPODS

(71) Applicant: The Government of the United States of America, as represented by the Secretary of the Navy, Arlington, VA (US)

(72) Inventors: Horn-Bond Lin, Las Vegas, NV (US); Matthew B. Hart, Silver Spring, MD (US); Jay D. Eversole, Woodbridge, VA (US); Keith W. Blount, Brooks City-Base, TX (US); Wesley Walker, Brooks City-Base, TX (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 262 days.

(21) Appl. No.: 15/798,488

(22) Filed: Oct. 31, 2017

(65) Prior Publication Data

US 2018/0049406 A1    Feb. 22, 2018

Related U.S. Application Data

(62) Division of application No. 14/210,897, filed on Mar. 14, 2014, now Pat. No. 9,832,972.

(60) Provisional application No. 61/786,770, filed on Mar. 15, 2013.

(51) Int. Cl.
*A01K 11/00*    (2006.01)
*B05B 5/053*    (2006.01)
*B05B 5/025*    (2006.01)
*A01K 67/033*   (2006.01)
*B05B 5/16*     (2006.01)

(52) U.S. Cl.
CPC .......... *A01K 11/005* (2013.01); *A01K 67/033* (2013.01); *B05B 5/0255* (2013.01); *B05B 5/0533* (2013.01); *B05B 5/1691* (2013.01)

(58) Field of Classification Search
CPC ... B05B 5/0255; B05B 5/0533; B05B 5/1691; A01K 11/00; A01K 11/005; A01K 13/003; A01K 67/033; G01N 15/0205
See application file for complete search history.

(56) References Cited

U.S. PATENT DOCUMENTS

| | | | |
|---|---|---|---|
| 6,399,362 B1* | 6/2002 | Pui | B01J 2/006 435/285.2 |
| 6,787,313 B2* | 9/2004 | Morozov | B01J 19/0046 435/6.12 |
| 2012/0226288 A1* | 9/2012 | Mays | A01K 11/00 606/116 |
| 2013/0304079 A1* | 11/2013 | Lin | A01K 11/005 606/116 |

* cited by examiner

*Primary Examiner* — Alex M Valvis
(74) *Attorney, Agent, or Firm* — US Naval Research Laboratory; Rebecca L. Forman

(57) ABSTRACT

Disclosed is an apparatus and associated method for tagging insects and arthropods. According to an exemplary embodiment of this disclosure, an electrosprayer is provided including a nozzle cartridge, a spray chamber removably attached to the nozzle cartridge and a power supply operatively connected to the nozzle cartridge and a grounding plate within the spray chamber to electrically charge droplets expelled from the nozzle which coat one or more insects contained in the spray chamber.

8 Claims, 4 Drawing Sheets

METHOD FOR TAGGING INSECTS AND ARTHROPODS

PRIORITY CLAIM

Figure 1:
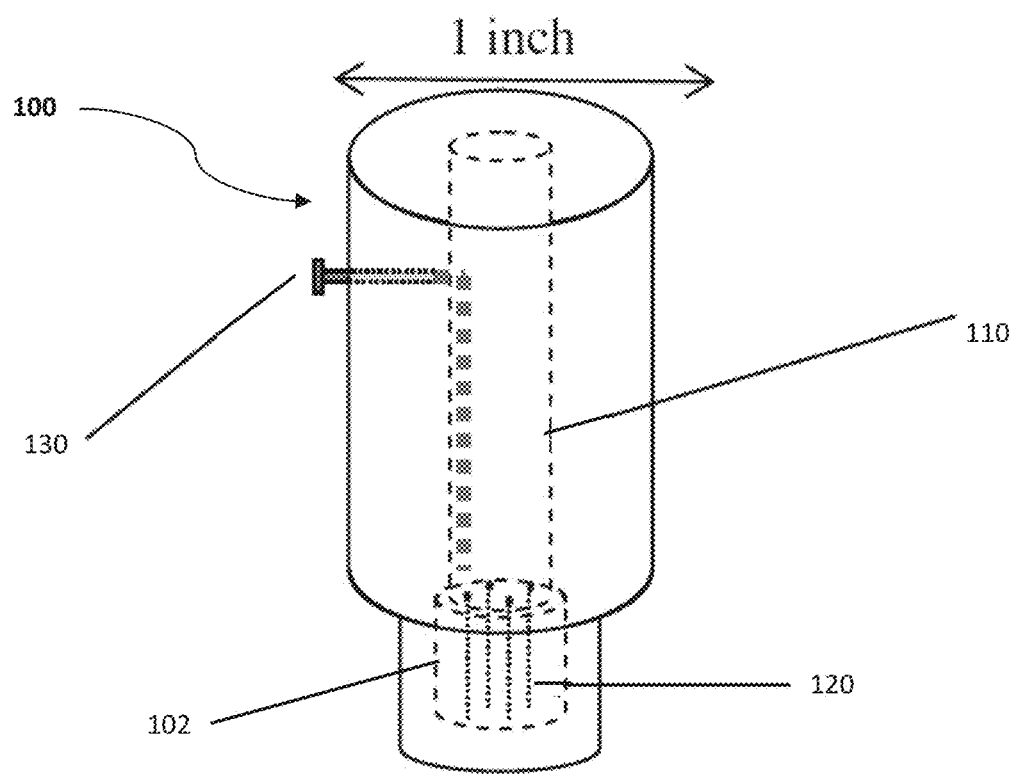

The present application is a divisional of U.S. application Ser. No. 14/210,897, filed on Mar. 14, 2014, which is a non-provisional application claiming the benefit of U.S. Provisional Application No. 61/786,770, filed on Mar. 15, 2013 by Horn-Bond Lin et al., entitled "ELECTROSPRAYER FOR ARTHROPOD TAGGING." The entire contents of these applications are incorporated herein by reference.

BACKGROUND OF THE INVENTION

Field of the Invention

The present invention relates generally to insect and arthropod tagging and, more specifically, to tagging using an electrosprayer.

Description of the Prior Art

A reliable method for tagging insects (and other potential appropriate arthropods, such as scorpions, spiders, etc., hereinafter simply referred to as "insects") is a key component in studies of their biology, ethology, and demography. Reliable and effective methods depend on a device that can consistently deliver the tagging material onto the target insects efficiently. Devices are needed to tag insects with marking agents that include: fluorescent dyes, quantum dots, molecular beacons or aptamers and proteins, and magnetic particles. Moreover, the devices need to tag insects in a short period of time, i.e., within a few seconds to a minute to avoid over-stressing the organism.

Current insect tagging devices utilize nebulization to create and apply liquid droplets for coating. This method is relatively ineffective because the bodies of insects are typically covered with hairs or bristles (setae) that are dense enough to prevent droplets larger than about 50 microns from reaching the exoskeleton below. In this fashion, the bristles on the insect's body act as a hydrophobic barrier for protection, shielding the subject from foreign materials such as rain, mist, and small debris. Nebulization methods of droplet creation typically produce droplets too large to penetrate this protective barrier. When using these methods, excessive wetting of the insects usually results from efforts to compensate for the lack of penetration of the droplets. This is not only wasteful of potentially expensive reagent solutions, but can leave such high amounts of fluid on the insects so as to incapacitate and/or harm them, while still failing to provide a satisfactory coating.

BRIEF SUMMARY OF THE INVENTION

The aforementioned problems are overcome in the present invention which provides an electrosprayer for insect and arthropod tagging having a nozzle cartridge comprising a liquid reservoir, a high voltage connector, and at least one nozzle; a spray chamber where each nozzle is directed into the spray chamber; and a high voltage power supply, where the power supply applies voltage through the high voltage connector. Also disclosed is the related method for tagging insects and arthropods.

The present invention pertains generally to the use of an electrospray, chamber device used for the labeling of arthropods (insects) with specific tagging agents including fluorescence dyes, quantum dots, magnetic metallic particles, molecular proteins, and biological binding materials. The invention relates to an apparatus that is capable of generating charged droplets that are sub-micrometer or even nanometer in size for efficient topical coating (tagging) of insects. The ability to spray-coat (tag) insects in a consistent manner using these materials is useful over a broad spectrum of sciences. Behavior monitoring and forensic studies are two examples of areas that benefit from the tagging of insects.

The electrospray device of the present invention produces droplets that can range in size from nanometers up to a few micrometers. This size range of droplets more easily penetrates between the body bristles to the exoskeleton underneath. Additionally, the electrospray process places a substantial amount of static charge onto the surface of the droplets. This charge is beneficial since it attracts the droplets to the insect body for better adhesion. Additionally, once the droplets are placed onto the subjects' body beneath the bristles, they are protected from washing or being bumped off; thus creating a more permanent method of tagging. Electrosprays operate at low mass flow rates that will not be mechanically violent to smaller subjects such as gnats, mosquitoes, etc. Flow rates typically are less than 5 μl/min (compared to about 1 ml/min [200 times greater] for typical nebulizers). This has the additional advantage that a quantity of about 5 ml of tagging solution could be continuously sprayed for more than 16 hours. Due to the higher efficiency of the smaller droplets from an electrospray, both the amount of material needed and the exposure time (less than 5 seconds in typical cases) can be considerably reduced.

These and other features and advantages of the invention, as well as the invention itself, will become better understood by reference to the following detailed description, appended claims, and accompanying drawings.

BRIEF DESCRIPTION OF THE DRAWINGS

FIG. 1 is a schematic of an electrospray nozzle cartridge assembly.

FIGS. 2A and 2B are black-and-white photos showing a side view of the basic component of an electrospray cartridge (FIG. 2A), and a single nozzle cartridge seen from below (FIG. 2B).

FIG. 3 is a schematic of an insect electrospraying device.

FIG. 4 is a black-and-white microscope photo of an area on a fly wing after being electrosprayed with rhodamine 6G dye (left and lower). The image shows individual dye droplets much smaller than the setae and spaces between the setae (individual seta are approx. 100 microns in length).

DETAILED DESCRIPTION OF THE INVENTION

In view of the foregoing, it is therefore an object of the present invention to provide an effective sprayer device particularly useful for efficiently and effectively tagging insect subjects. It is a further object of the invention to provide a spraying apparatus that is capable of generating a charged solution into the chamber to coat insects with low concentrations and quantities of aerosol droplets. The solution comprises tagging agents or a mixture of tagging agents, such as fluorescent dyes, quantum dots, molecular beacons, aptamers, proteins, and aqueously suspended metallic particles. These and other objects of the invention are achieved via a liquid spraying device. The device components include: an electrospray nozzle cartridge, a high voltage power supply, a spraying chamber, and a laser for visually monitoring the electrospray operation.

Electrospray Nozzle Cartridge Assembly

Figure 2B:
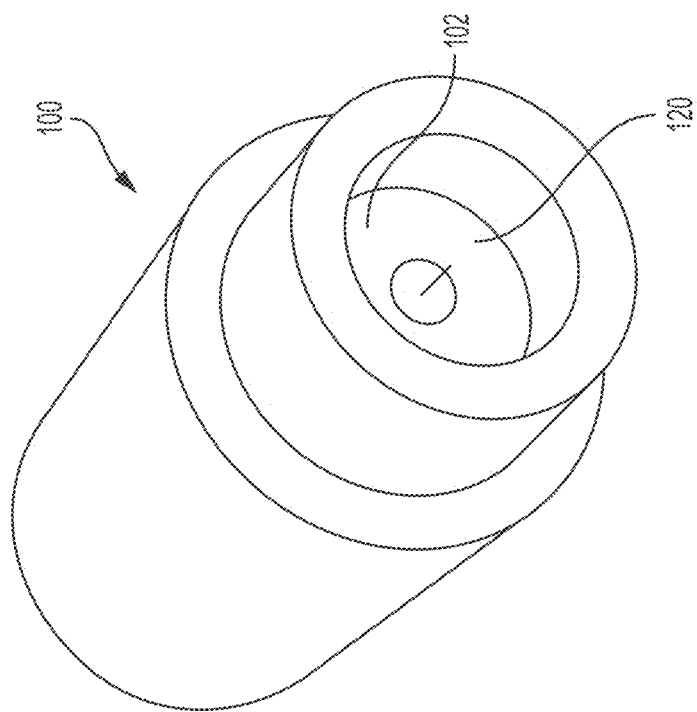
Figure 2A:
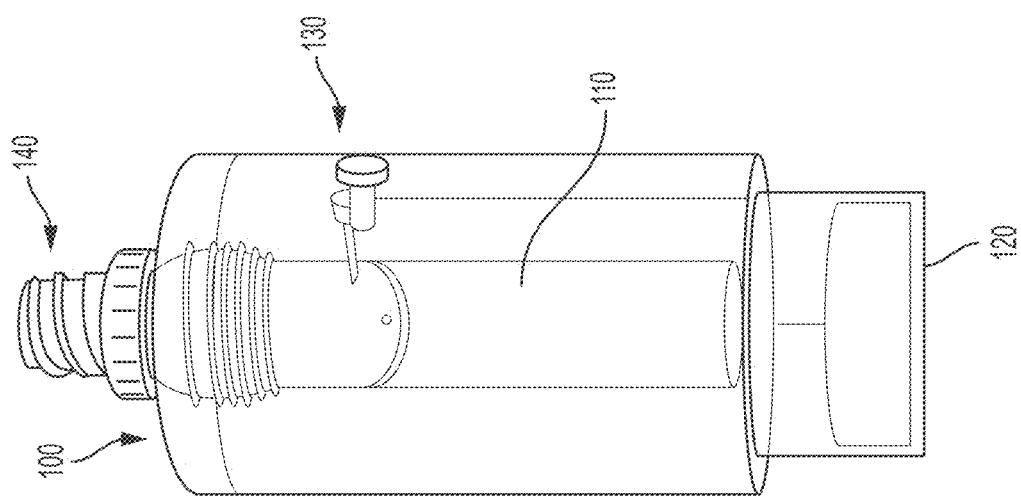

The nozzle cartridge 100 is shown in FIG. 1. In a preferred embodiment, it comprises a 1-inch diameter cylinder made of polypropylene plastic that forms a central liquid reservoir 110. This central liquid reservoir 110 supplies the (liquid) tagging solution to the electrospray nozzle(s) 120 located at the bottom of the nozzle cartridge. The cartridge holds the electrospray nozzle(s) 120 in place and accommodates an electric connector wire 130 to be attached to the high voltage source for the electrospraying operation. The volume for the reservoir is typically 1-5 ml. The number of electrospray nozzles 120 mounted at the bottom of each cartridge 100 provides control over the rate of application of tagging material. The design shown in FIG. 1 has been kept simple to reduce fabrication cost. Cartridges with varying number of nozzles and array configurations can be constructed while maintaining the overall dimensions of the piece. This establishes an interchangeable standardized part, permitting easy replacement in case of clogging or desired nozzle re-configurations (e.g., for application rate changes). FIGS. 2A and 2B are two photos showing (FIG. 2A) a vertical view and (FIG. 2B) a bottom-end orientation showing a single electrospray nozzle.

In a preferred embodiment, the electrospray nozzles 120 are created from a ¾" length section of silica capillary tubing. The outside diameter (O.D.) of this tubing is 360 micrometers, and can have various inside diameters (I.D.) ranging from 25 to 150 micrometers. To mount an electrospray nozzle 120, a hole matching the O.D. is bored into the bottom of a cartridge 100. An electrospray nozzle 120 is inserted into the hole, so that the capillary tubing protrudes slightly above the inside bottom of the reservoir, and is fixed with adhesive applied to the outside surface. The central section of the cartridge 102 will have been counter-bored, or inset, so that the nozzles 120 do not protrude below the end of the cartridge body. This serves to protect the nozzle tips while allowing the cartridge 100 to be placed upright on a flat surface.

A common syringe connector 140 (e.g. Luer Lock) can be built into the top end of the cartridge 100 so that a syringe can be used to inject liquid solution into the reservoir 110 and to provide a pressure to prime the nozzle(s) at the beginning of operation, just prior to the application of the high voltage (HV) to begin the electrospray. A direct current (DC) HV (typically in the range of 2.5-10 kilovolts) is applied through the embedded HV connector 130 that is tapped into the side-wall of the cartridge 100. A very fine spray of submicron droplets will result from the nozzle(s) 120 at the bottom of the cartridge 100 when these conditions are met.

These standardized interchangeable cartridges 100 can be easily inserted into the top section of the Head Assembly as described in the following paragraphs.

Head Assembly

The head assembly 10 comprises a top section 200 and the nozzle cartridge assembly 100 (described above) as shown in FIG. 3. In a preferred embodiment, a standardized, commercially available high voltage connector 230 is built into the top section 200. When the nozzle cartridge 100 is inserted into the top section 200, the high voltage connector 230 built into the top section 200 makes electrical contact with the customized high voltage connector 130 on the nozzle cartridge 100 to complete the circuit for electrospray operation.

Spray Chamber

The spray chamber 20 provides a confinement space for tagging the insect subjects. A bottom portion 210 of the head assembly fits into a top portion 310 of the spray chamber. The floor 400 of the spray chamber 20 is an electrically grounded conducting plate 410 required for electrospray operation. In a preferred embodiment, the spray chamber 20 is cylindrical in shape and made of transparent plastic such as Lucite with optical windows built into the sides. Two of these windows 302 and 304 should be diametrically opposed to permit the laser beam to propagate through the center of the chamber 20 and illuminate the electrospray plume when in operation. A third window (not shown) can be used for viewing the laser light scattered by the spray droplets.

Chamber Body

Figure 3:
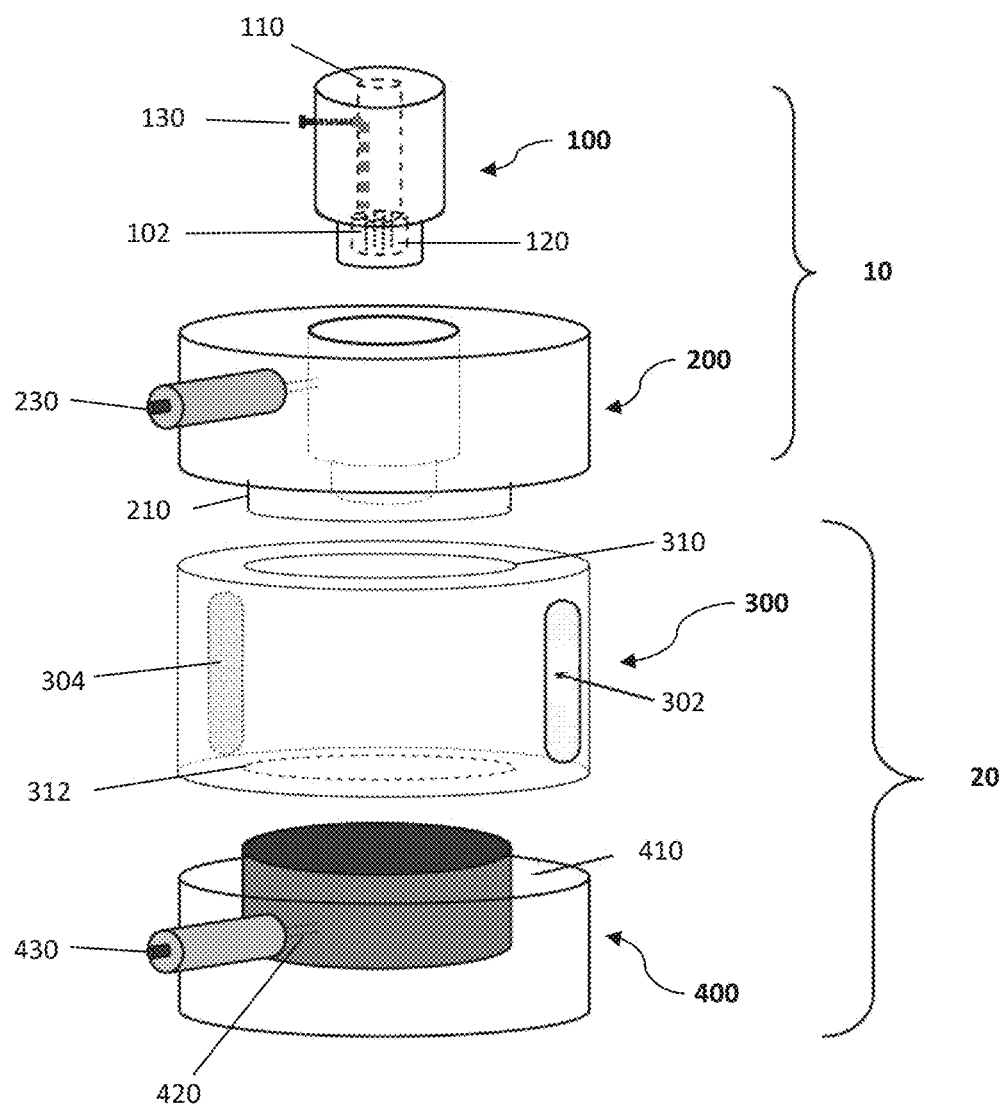

FIG. 3 shows the chamber body 300 as a transparent, cylindrical tube of Lucite. While FIG. 3 is not to scale, typical dimensions are 2 inches (diameter)×1/8 inches (thickness)×2 inches (height). There are three openings cut to accommodate three optical windows. The diametrically opposed pair of windows 302 and 304 is centered top to bottom and is about 1 inch long. A third, viewing window may be placed at an arbitrary angle.

Bottom Plate

The bottom plate 400 comprises a Lucite plate imbedded with a metal grounding plate 410. The circular metal (aluminum or copper) grounding plate 410 is ¼-inch thick, and serves as an electrical ground for the electrospray. The grounding plate 410 diameter matches the chamber body 300 inside diameter 312. The upper part of the Lucite bottom plate 400 is bored out to match the metal ground plate 410 diameter. Its function is to isolate the grounding plate 410 from any contact with the surroundings for safety reasons. The grounding plate 410 is accessed for connection to the ground connector 430 through a hole 420 drilled through the side of the Lucite plate. This permits a metal rod (not shown) to connect the grounding plate 410 to an outside high voltage connector 430. A standardized commercial high voltage connector 430 of the opposite polarity to the top section 200 is then connected to this metal rod and attached to the bottom plate 400.

High Voltage DC Power Supply

A commercial power supply capable of providing up to 10 kilovolts of DC voltage is required (not shown). During operation, the current from a typical electrospray has been found to be less than 100 nanoamperes, so a low current power supply is adequate, and recommended for safety considerations.

Typical Operation

Electrospray

For operating the electrospray, there are several steps to follow. With a filled cartridge 100 in place, connect the high voltage source to the HV connector 130 on the top section. Using the laser to illuminate the area just below the nozzle cartridge 100, gradually dial the voltage up until the spray action is observed. If the voltage has reached the maximum voltage that the power supply can provide and no spray action is observed, turn the voltage down to zero and wait for a minute to allow discharge of any residual voltages. Then place an air-filled syringe onto the syringe adapter 140 on the top of cartridge 100 and push the syringe to squeeze some liquid out of the nozzle tip(s) 110 to ensure a capillary is not clogged. Turn on the voltage and repeat again until the spraying occurs.

Insect Spraying

With the high voltage source turned off and disconnected from the device, pull out the head assembly 10 from the sprayer chamber 20 and drop the insect(s) for tagging through the opening from the top into the chamber. Replace the assembly top 10. After connecting the HV wire gradually increase the HV power source and watch the spray action through the viewing window until the spray is going steadily as described above. Typical spraying times are a few seconds, but may need to be adjusted depending on the type and number of insects being tagged. After spraying, turn the voltage and the laser off, and wait for at least one minute to allow any residual static charges to dissipate. Pull off the head assembly 10 to retrieve the sprayed insect(s).

Figure 4:
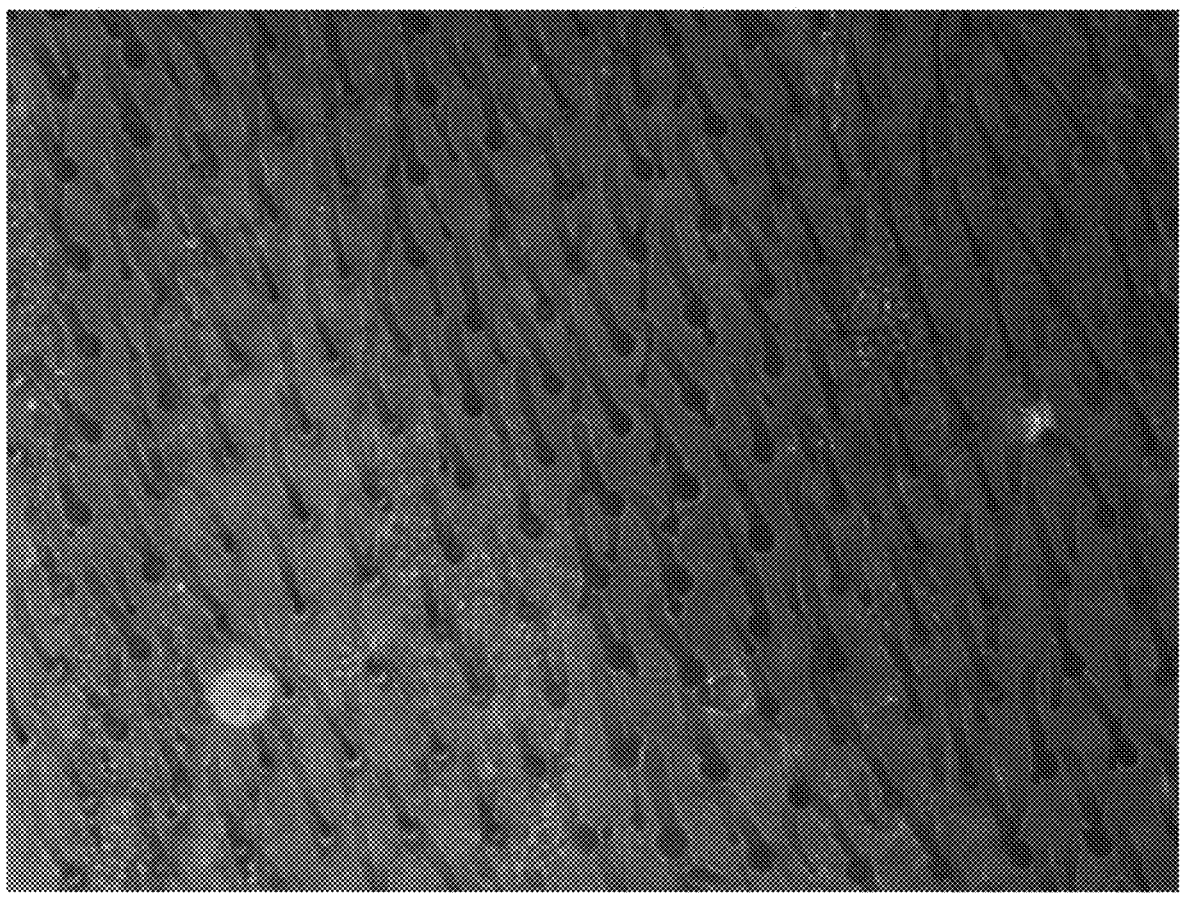

As an illustration of the technique, FIG. 4 is a microscopic image of a blow fly wing in which the left lower diagonal area has been electrosprayed with a dye. This area shows a nearly uniform coating, compared to the normal uncoated wing area in the upper right. In this particular case, the dye used was an aqueous solution of rhodamine 6G.

In the description of this invention specific dimensions have been listed. These specific dimensions are not required to produce the desired effect of properly tagging insects. Constraints on the volume of the chamber 100 are only such that the insects are not further than approximately 2 inches from the spray nozzles 110. The one inch diameter of the spray cartridges 100 has been used in the development due to convenience, since various off-the-shelf supports use this dimension. The specific material the apparatus is created from is not needed to be the same as listed here, but does need to be electrically nonconductive.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed is:

1. A method for tagging a subject, comprising:
    adding a tagging agent into a reservoir of a nozzle cartridge, wherein the nozzle cartridge also comprises a first electrical connector and at least one nozzle, wherein the at least one nozzle is operatively associated with the reservoir and inserted through at least one hole in a bottom end of the nozzle cartridge, wherein the at least one nozzle does not protrude below the bottom end of the nozzle cartridge, and wherein the first electrical connector is operatively connected to one of the reservoir and the at least one nozzle;
    adding the subject into a spray chamber, wherein the spray chamber comprises a chamber body, a spray chamber bottom plate comprising a rounding plate and a second electrical connector operatively connected to the grounding plate, wherein the chamber body is adapted to form a confinement space for tagging a subject provided therein, and wherein the grounding plate is adapted to substantially cover a bottom portion of the spray chamber opposite a top portion of the spray chamber;
    inserting the nozzle cartridge into a top section of a head assembly, wherein the head assembly is adapted to be removably attached to a top portion of the spray chamber, wherein the nozzle cartridge is removably inserted into the top section of the head assembly, and wherein the head assembly is adapted to direct the at least one nozzle into the top portion of the spray chamber;
    connecting a high voltage source to provide a voltage and current across the first electrical connector and the second electrical connector, thereby charging droplets of the tagging agent within the reservoir; and
    spraying the subject with charged droplets of the tagging agent expelled from that at least one nozzle and directed to the grounding plate.

2. The method of claim 1, wherein the nozzle cartridge has a top end comprising a syringe connector.

3. The method of claim 1, additionally comprising a laser configured to light an area below the nozzle cartridge within the spray chamber wherein the spray chamber includes two diametrically opposing openings to allow the laser beam to propagate through the spray chamber.

4. The method of claim 3, wherein the spray chamber includes a third opening to view the laser light.

5. The method of claim 1, wherein the high voltage source is configured to apply ten kilovolts or less of voltage.

6. The method of claim 1, wherein the tagging agent comprises a fluorescent dye, quantum dots, molecular beacons, aptamers, proteins, aqueously suspended metallic particles, or any combination thereof.

7. The method of claim 1, wherein the subject is an arthropod.

8. The method of claim 1, wherein at least a portion of the subject is coated with the tagging agent.

* * * * *